United States Patent [19]
Iggo et al.

[11] Patent Number: 5,744,303
[45] Date of Patent: Apr. 28, 1998

[54] FUNCTIONAL ASSAY FOR TRANSCRIPTIONAL REGULATOR GENES

[75] Inventors: Richard Iggo, Epalinges, Switzerland; Stephen H. Friend, Concord, Mass.; Thierry Frebourg, Rouen, France; Chikashi Ishioka, Bookline, Mass.

[73] Assignees: The General Hospital Corporation, Boston, Mass.; Institut Suisse de Recherches Experimentales, Switzerland

[21] Appl. No.: 447,179

[22] Filed: May 22, 1995

Related U.S. Application Data

[63] Continuation of Ser. No. 46,033, Apr. 12, 1993, abandoned, which is a continuation-in-part of Ser. No. 956,696, Oct. 1, 1992, abandoned.

[51] Int. Cl.$^6$ .................. C12Q 1/68; C12P 19/34
[52] U.S. Cl. .................. 435/6; 435/7.1; 435/91.2; 435/69.1; 435/71.1; 435/172.3
[58] Field of Search ........... 435/6, 7.1, 91.2, 435/69.1, 71.1, 172.3, 254.2, 254.21; 935/36, 37

[56] References Cited

U.S. PATENT DOCUMENTS

| | | | |
|---|---|---|---|
| 4,942,123 | 7/1990 | Lee et al. | 435/6 |
| 4,981,784 | 1/1991 | Evans et al. | 435/6 |
| 4,997,757 | 3/1991 | Schiestl | 435/172.1 |
| 5,011,773 | 4/1991 | Lee et al. | 435/69.1 |
| 5,183,736 | 2/1993 | Pfahl et al. | 435/6 |
| 5,362,623 | 11/1994 | Vogelstein et al. | 435/6 |

FOREIGN PATENT DOCUMENTS

| | | |
|---|---|---|
| 0 259 031 | 3/1988 | European Pat. Off. |
| 0 293 266 | 11/1988 | European Pat. Off. |
| 0 390 323 | 10/1990 | European Pat. Off. |
| WO 88/09387 | 1/1988 | WIPO |

OTHER PUBLICATIONS

Guarente, *Cell* 52, 303–305 (1988).
Guthrie et al., eds., *Meth. Enzymol.* 194, 373–398 (1991).
Frebowry et al., *Cancer Res.* 52 6976–6978 (1992).
Ishioka et al., *Nature Gen.* 5, 124–129 (1993).
Baker et al., Science 249:912–915 (1990), "Suppression of Human Colorectal Carcinoma Cell Growth by Wild–Type p53".
Bressac et al., Nature 350:429–431 (1991), "Selective G to T mutations of p53 gene in hepatocellular carcinoma from southern Africa".
Børresen et al., Cancer Research 52:3234–3236 (1992), "Screening for Germ Line TP53 Mutations in Breast Cancer Patients".
Børresen et al., Proc. Natl. Acad. Sci. USA 88:8405–8409 (1991), "Constant denaturant gel electrophoresis as a rapid screening technique for p53 mutations".

(List continued on next page.)

*Primary Examiner*—Kenneth R. Horlick
*Attorney, Agent, or Firm*—Fish & Richardson P.C.

[57] ABSTRACT

A method for determining whether an individual, i.e., a human, carries a mutation in a gene which encodes a transcriptional regulator (e.g., a tumor suppressor). The method includes the steps of obtaining a nucleic acid sample comprising cDNAs encoding both alleles of the gene from a cell sample from the individual; providing a nucleic acid construct comprising a binding site operably linked to DNA encoding a detectable protein such that transcription of the DNA encoding the detectable protein is regulated by interaction of the transcriptional regulator polypeptide with the binding site; transfecting the nucleic acid sample and the nucleic acid construct into cells with low levels of the transcriptional regulator polypeptide; and then determining the levels of the detectable protein in the transfected cells, this level being correlated with the presence of a mutation in at least one of the alleles of the gene.

31 Claims, 4 Drawing Sheets

OTHER PUBLICATIONS

Cance et al., The New England Journal of Medicine 323:1457–1462 (1990), "Altered Expression of the Retinoblastoma Gene Product in Human Sarcomas".

Cotton et al., Proc. Natl. Acad. Sci. USA 85:4397–4401 (1988), "Reactivity of cytosine and thymine in single-base-pair mismatches with hydroxylamine and osmium tetroxide and its application to the study of mutations".

Dalbagni et al., Proceedings of the AACR 33:373, Abstract π2229 (1992), "P53 and chromosome 17 abnormalities in human bladder tumors".

Diller et al., Molecular and Cellular Biology 10:5772–5781 (1990), "p53 Functions as a Cell Cycle Control Protein in Osteosarcomas".

El-Diery et al., Nature Genetics 1:45–49 (1992), "Definition of a consensus binding site for p53".

Farmer et al., Nature 358:83–86 (1992), "Wild-type p53 activates transcription in vitro".

Fields et al., Science 249:1046–1048 (1990), "Presence of a Potent Transcription Activating Sequence in the p53 Protein".

Frebourg et al., Proc. Natl. Acad. Sci. USA 89:6413–6417 (1992), "Germ-Line mutations of the p53 tumor suppressor gene in patients with high risk for cancer inactivate the p53 protein".

Funk et al., Molecular and Cellular Biology 12:2866–2871 (1992), "A Transcriptionally Active DNA-Binding Site for Human p53 Protein Complexes".

Hsu et al., Nature 350:427–428 (1991), "Mutational hotspot in the p53 gene in human hepatocellular carcinomas".

Iavarone et al., Proc. Natl. Acad. Sci. USA 89:4207–4209 (1992), "Germ-line and somatic p53 gene mutations in multifocal osteogenic sarcoma".

Kern et al., Science 256:827–830 (1992), "Oncogenic Forms of p53 Inhibit p53-Regulated Gene Expression".

Kern et al., Science 252:1708–1711 (1991), "Identification of p53 as a Sequence-Specific DNA-Binding Protein".

Law et al., Cancer Research 51:6385–6387 (1991), "A Germ Line Mutation in Exon 5 of the p53 Gene in an Extended Cancer Family".

Lee et al., Nature 329:642–645 (1987), "The retinoblastoma susceptibility gene encodes a nuclear phospho-protein associated with DNA binding activity".

Li et al., Journal of the National Cancer Institute 84:1156–1160 (1992), "Recommendations on Predictive Testing for Germ Line p53 Mutations Among Cancer-Prone Individuals".

Madden et al., Science 253:1550–1553 (1991), "Transcriptional Repression Mediated by the WT1 Wilms Tumor Gene product".

Malkin et al., The New Eng. J. of Medicine 326:1309–1315 (1992), "Germline Mutations of the p53 Tumor-Suppressor Gene in Children and Young Adults with Second Malignant Neoplasms".

Malkin et al., Science 250:1233–1238 (1990), "Germ Line p53 Mutations in a Familial Syndrome of Breast Cancer, Sarcomas, and Other Neoplasms".

Metzger et al., Proc. Natl. Acad. Sci. USA 88:7825–7829 (1991), "Identification of a germ-line mutation in the p53 gene in a patient with an intracranial ependymoma".

Raycroft et al., Science 249:1049–1051 (1990), "Transcriptional Activation by Wild-Type But Not Transforming Mutants of the p53 Anti-Oncogene".

Romano et al., Oncogene 4:1483–1488 (1989), "Identification and characterization of a p53 gene mutation in a human osteosarcoma cell line".

Santibanez-Korff et al., The Lancet 338:1490–1491 (1991), "p53 germline mutations in Li-Fraumeni syndrome".

Sarkis et al., Proc. Am. Assoc. Cancer Res. 33:254 (1992), "p53 Mutations as a Predictor of Biological Behavior of T1 Bladder Carcinoma".

Sidransky et al., Cancer Research 52:2984–2986 (1992), "Inherited p53 Gene Mutations in Breast Cancer".

Srivastava et al., Nature 348:747–749 (1990), "Germ-line transmission of a mutated p53 gene in a cancer-prone family with Li-Fraumeni syndrome".

Thor et al., Journal of the Natl. Cancer Inst. 84:845–855, 1992 "Accumulation of p53 Tumor Suppressor Gene Protein: An Independent Marker of Prognosis in Breast Cancers".

Toguchida et al., New Engl. J. Med. 326:1301–1308 (1992).

Vogelstein, Nature 348:681–682 (1990), "A deadly inheritance".

Schärer et al., Nucleic Acids Research 20:1539–1545 (1992), "Mammalian p53 can function as a transcription factor in yeast."

Donehower et al., Nature 356:215–221 (1992), "Mice deficient for p53 are developmentally normal but susceptible to spontaneous tumours."

Hurwitz et al., The American Journal of Surgery 164:299–306 (1992), "Diagnostic and Prognostic Molecular Markers in Cancer."

Weintraub et al., Proc. Natl. Acad. Sci. USA 88:4570–4571 (1991), "The MCK enhancer contains a p53 responsive element".

FIG. 6

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
    ( A ) LENGTH: 48
    ( B ) TYPE: nucleic acid
    ( C ) STRANDEDNESS: single
    ( D ) TOPOLOGY: linear ( x i ) SEQUENCE DESCRIPTION: SEQ ID NO: 1:

GGAATTCCTT GCCTTGCCTG GACTTGCCTG GCCTTGCCTT GGAATTCC             48

( 2 ) INFORMATION FOR SEQ ID NO: 2:

( i ) SEQUENCE CHARACTERISTICS:
    ( A ) LENGTH: 34
    ( B ) TYPE: nucleic acid
    ( C ) STRANDEDNESS: single
    ( D ) TOPOLOGY: linear ( x i ) SEQUENCE DESCRIPTION: SEQ ID NO: 2:

AGTCAAGCTT GACGGTGACA CGCTTCCCTG GATT                            34

( 2 ) INFORMATION FOR SEQ ID NO: 3:

( i ) SEQUENCE CHARACTERISTICS:
    ( A ) LENGTH: 34
    ( B ) TYPE: nucleic acid
    ( C ) STRANDEDNESS: single
    ( D ) TOPOLOGY: linear ( x i ) SEQUENCE DESCRIPTION: SEQ ID NO: 3:

AGTCTCTAGA TCAGTGGGGA ACAAGAAGTG GAGA                            34

( 2 ) INFORMATION FOR SEQ ID NO: 4:

( i ) SEQUENCE CHARACTERISTICS:
    ( A ) LENGTH: 55
    ( B ) TYPE: nucleic acid
    ( C ) STRANDEDNESS: single
    ( D ) TOPOLOGY: linear ( x i ) SEQUENCE DESCRIPTION: SEQ ID NO: 4:

CCCCGGATCC ACTAGAAATA ATTTTGTTTA ACTTAAGAA GGAGATATAC GC          52

ATG                                                              55
Met

1

( 2 ) INFORMATION FOR SEQ ID NO: 5:

( i ) SEQUENCE CHARACTERISTICS:

```
              ( A ) LENGTH: 8
              ( B ) TYPE: nucleic acid
              ( C ) STRANDEDNESS: single
              ( D ) TOPOLOGY: linear ( x i ) SEQUENCE DESCRIPTION: SEQ ID NO: 5:

CCCCTCGA                                                                              8

( 2 ) INFORMATION FOR SEQ ID NO: 6:

( i ) SEQUENCE CHARACTERISTICS:
              ( A ) LENGTH: 38
              ( B ) TYPE: nucleic acid
              ( C ) STRANDEDNESS: double
              ( D ) TOPOLOGY: linear ( x i ) SEQUENCE DESCRIPTION: SEQ ID NO: 6:

TCGACCTTGC  CTGGACTTGC  CTGGCCTTGC  CTTTTCGA                                         38

( 2 ) INFORMATION FOR SEQ ID NO: 7:

( i ) SEQUENCE CHARACTERISTICS:
              ( A ) LENGTH: 25
              ( B ) TYPE: nucleic acid
              ( C ) STRANDEDNESS: single
              ( D ) TOPOLOGY: linear ( x i ) SEQUENCE DESCRIPTION: SEQ ID NO: 7:

TGGATTGGCA  GCCAGACTGC  CTTCC                                                        25

( 2 ) INFORMATION FOR SEQ ID NO: 8:

( i ) SEQUENCE CHARACTERISTICS:
              ( A ) LENGTH: 25
              ( B ) TYPE: nucleic acid
              ( C ) STRANDEDNESS: single
              ( D ) TOPOLOGY: linear ( x i ) SEQUENCE DESCRIPTION: SEQ ID NO: 8:

GTGGGAGGCT  GTCAGTGGGG  AACAA                                                        25
```

FUNCTIONAL ASSAY FOR TRANSCRIPTIONAL REGULATOR GENES

This is a continuation of application Ser. No. 08/046,033, filed Apr. 12, 1993, now abandoned which is a continuation-in-part of application Ser. No. 17/956,696 filed Oct. 1, 1992, abandoned.

This invention was made with Government support under Contract #CA-55898 awarded by the National Institutes of Health. The Government has certain rights in this invention.

BACKGROUND OF THE INVENTION

The present invention relates to methods for detecting the presence of mutations in genes which encode transcriptional regulators, and more particularly tumor suppressor genes.

Tumor suppressor genes have been postulated to encode proteins that regulate normal growth, and thus indirectly suppress neoplastic development. In cells, these genes appear to act recessively, so that both maternal and paternal alleles of the gene product must be inactivated in order for the suppressor function to be eliminated. Thus, current theories suggest that germline mutations in tumor suppressor genes represent a genetic predisposition for cancer development.

The gene for the nucleophosphoprotein p53 is the most commonly mutated tumor suppressor gene yet identified in human cancers (Volgelstein, *Nature* 348:681, 1990). Germline p53 mutations were initially identified in the Li-Fraumeni syndrome (LFS), an autosomal dominant cancer syndrome characterized by the development of different malignancies including breast cancers, sarcomas and central nervous system tumors (Malkin et al., *Science* 250:1233, 1990; Srivastava et al., *Nature* 348:747, 1990; Law et al., *Cancer Res.* 51:6385, 1991; Santibanez-Koref et al., *Lancet*:338:1490, 1991; Li et al., *J. Natl. Cancer Inst.* 84:1156, 1992). The cancer risk for germline p53 mutation carriers in some LFS families has been estimated to be 50% by 30 years of age and to 90% by 60–70 years of age (Santibanez-Koref et al., supra). Germline p53 mutations have also been identified, outside the LFS, in patients who had developed multiple primary cancers (Malkin et al., *New Engl. J. Med.* 326:1309, 1992; Toguchida et al., *New Engl. J. Med.* 326:1301, 1992) and in patients with sarcomas (Toguchida et al., supra; Iavarone et al., *Proc. Natl. Acad. Sci. USA* 89:4207, 1992), brain tumors (Metzger et al., *Proc. Natl. Acad. Sci. USA*, 88:7825, 1991), or breast cancers (Sidransky et al., *Cancer Res.* 52:2984, 1992; Borresen et al., *Cancer Res.* 52:3234, 1992). Hence, the identification of individuals who carry germline mutations in p53, as well as other tumor suppressor genes, is of critical importance in order to monitor those individuals who are at increased risk for developing cancer, since the morbidity and mortality of most cancers is significantly reduced if diagnosis can be made during early onset of the disease.

At the present time, detection of mutations in the p53 gene, as well as other genes associated with cancer susceptibility, requires a significant effort because the germline mutations detected thus far have been shown to be widely distributed throughout the gene. There are several nucleic acid-based techniques that can detect mutations within short fragments of DNA. These techniques include sequencing of the genomic region encoding the gene, RNAse protection assays, detection of base-pair mismatches with hydroxylamine and osmium tetroxide, and methods such as CDGE (Constant Denaturant Gel Electrophoresis) (Malkin et al., supra; Borresen et al., supra), DGGE (Denaturing Gradient Gel Electrophoresis) (Metzger et al., supra), and SSCP (Single Strand Conformation Polymorphism) (Toguchida et al., supra; Iavarone et al., supra) which are based on the modification of the DNA conformation induced by mutations. The hydroxylamine/osmium tetroxide technique does not detect A to T or T to A changes (Cotton et al., *Proc. Natl. Acad. Sci. USA* 85:4397, 1988). RNase mismatch analysis requires the use of RNA. In the CDGE, DDGE, and SSCP techniques, the number of melting domains that can easily be resolved into one fragment is limited, and therefore surveys using these methods have concentrated on highly conserved domains of the gene being analyzed. One further drawback of all of these methods is that they are not capable of distinguishing inactivating mutations from previously unknown genetic polymorphisms or mutations that do not affect biological function.

Germline p53 mutations which produce no detectable biological effect have been observed (Frebourg et al., *Proc. Natl. Acad. Sci. USA* 89:6413, 1992). Thus, there is a need for methods which allow screening of individuals for germline mutations which provide an analysis of the transcriptional regulatory activity of a tumor suppressor gene product in order to correctly determine whether a particular germline mutation is associated with cancer risk.

SUMMARY OF THE INVENTION

In general, the invention features a method for determining whether an individual, i.e., a human, carries a mutation in a gene which encodes a polypeptide which is a transcriptional regulator. The method includes the steps of obtaining a first nucleic acid comprising a cDNA encoding the polypeptide from a cell sample from the individual, providing a second nucleic acid comprising a binding site operably linked to DNA encoding a detectable protein such that transcription of the DNA encoding the detectable protein is regulated by interaction of the polypeptide with the binding site, transfecting these first and second nucleic acids into cells with low levels of the polypeptide, and then examining the transfected cells for the level of the detectable protein, the level being correlated with the presence of a mutation in at least one of said alleles of said gene.

The cDNA encoding the transcriptional regulator polypeptide can be obtained from any cell sample containing normal cells. By "normal cells" is meant any nucleated cells which are not tumor cells. Preferably the cell sample is a blood sample, but may also be a urine or skin sample. Alternatively, the cDNA is obtained from a cell sample containing tumor cells. Tumor cell samples may be obtained by standard methods well known to those skilled in the art (e.g., surgical biopsy of neoplastic tissue). The cDNA may be generated from the DNA or RNA of the cells by any standard method. Preferably the cDNA is generated by a technique which combines reverse transcription of the cellular mRNA with polymerase chain reaction (PCR) such as those described herein.

The binding site of the second nucleic acid comprises DNA sequences which interact specifically with the transcriptional regulator polypeptide. This interaction may be characterized by either direct or indirect binding of the polypeptide to the binding site, but most preferably, the polypeptide binds directly to the DNA of the binding site. In indirect binding, the polypeptide binds not to the binding site, but to another entity (generally a protein) which binds to the binding site in a manner which is affected by the polypeptide. The binding sites for the polypeptides produced by the p53, Rb, and WT1 tumor suppressor genes are known (Madden et al., *Science* 253:1550; Kern et al., *Science* 253:1708, 1991; Lee et al., *Nature* 329:642, 1987), and may be provided as a synthetic oligonucleotide or obtained by standard cloning techniques. Identification of the DNA sequences contained within the binding sites of other genes involved in transcriptional regulation may also be achieved by standard methods such as DNA footprinting (see, e.g., Ausebel et al. *Current Protocols in Molecular Biology*, John Wiley & Sones, New York, hereby incorporated by reference) and CASTing (Wright et al., Mol. Cell Biol. 11:4104, 1991; Chittenden et al., Cell 65:1073, 1991; Funk et al., Mol. Cell Biol., 12:2866, 1992, hereby incorporated by reference).

The detectable protein used in the method of the invention may be any desired protein; the particular protein is not critical. In one preferred embodiment, the protein chosen is an enzyme, such as β-galactosidase or chloramphenicol acetyl transferase, that is easily detected by standard assay techniques, e.g., by calorimetric assay. In another preferred embodiment, the detectable protein is an enzyme which confers resistance to an antibiotic, and the level of detectable protein is determined by the ability of cells to grow in the presence of the antibiotic. In still another preferred embodiment, the detectable protein is essential for the production, i.e., biosynthesis, of a substance (e.g., amino acid, vitamin, purine or pyrimidine) which is required for cell viability, and the level of detectable protein is determined by the ability of the transfected cell to grow in the absence of the substance.

By the term "operably linked" as used herein is meant that the binding site for the transcriptional regulator polypeptide is in proximity with the DNA encoding the detectable protein to allow transcriptional regulation of the DNA by the polypeptide. The interaction of the transcriptional regulator polypeptide with the binding site of the second nucleic acid may regulate transcription by acting to either activate or repress the transcription of the DNA encoding the detectable protein depending on the particular tumor suppressor gene being analyzed. Preferred transcriptional activators include p53, and preferred transcriptional repressors include the retinoblastoma gene (Rb) and the Wilm's tumor gene (WT1).

The cells used for transfection of the nucleic acids encoding the tumor suppressor polypeptide and detectable protein may be any eukaryotic cells with low levels of the active transcriptional regulator polypeptide, e.g., cells which contain lower amounts of functionally active polypeptide than cells which contain two wild-type alleles. Preferably, the cells are derived from tumor cell lines which have been previously demonstrated to contain homozygous inactivating mutations of the tumor suppressor gene, e.g., Saos-2 cells (ATCC No. HTB85). Even more preferably, the cells lack the polypeptide. Most preferably, the cells are yeast cells.

The first and second nucleic acids may be cotransfected into the cells, or may be transfected separately. In one example, the second nucleic acid may be transfected prior to the second nucleic acid to yield a cell line, or strain, with detectable protein that can be maintained indefinitely (e.g., in culture, or frozen stock); the second nucleic acid may be stably integrated into the genome or maintained on an autonomously replicating plasmid.

In one embodiment of the method of the invention, the level of detectable protein in the transfected cells is compared to a standard. Various types of standards, i.e., controls, include the level of detectable protein in cells containing two wild-type alleles of the gene; the level of detectable protein in cells containing only one wild-type allele of the gene; or the level of detectable protein in cells which lack a wild-type allele of the gene. In this embodiment, a difference in the level of detectable protein between the experimental sample and one or more of the standards is indicative that one of the alleles from the individual carries a mutation which decreases the transcriptional regulatory activity of the polypeptide. For example, in the instance wherein the wild-type polypeptide acts as a transcriptional activator, the level of detectable protein induced by the cDNA obtained from an individual who carries one non-functional allele would be expected to be lower than the homozygous wild-type standard. Conversely, if the polypeptide normally acts as a transcriptional repressor, the level of detectable protein induced by the nucleic acid obtained from an individual with one non-functional allele would be expected to be higher than the homozygous wild-type standard.

In a second embodiment of the method of the invention, the alleles of the transcriptional regulator gene are separated prior to transfection, and each allele is transfected into different cells. In this embodiment, a difference in the level of detectable protein in cell samples containing different alleles of the gene is indicative that one of the alleles carries a mutation which decreases the transcriptional regulatory activity of the polypeptide. The alleles are preferably separated by cloning the cDNA containing both alleles into eukaryotic expression vectors to produce two vectors, each of which contains only one of the alleles.

In still another embodiment of the method of the invention, the first nucleic acid is stably transfected into a yeast cell by homologous recombination. Preferably, the cDNA encoding both of the alleles of the transcriptional regulatory gene is cotransfected into the yeast cells with a gap excision repair vector under conditions which promote homologous recombination between the cDNA and the vector such that only vectors containing the cDNA are stably maintained in the cell. Most preferably, the vector further contains a centromere thus producing cells with only one allele of the transfected cDNA.

Unless defined otherwise, all technical terms and scientific terms used herein have the same meaning as commonly understood by one of ordinary skill in the art to which this invention pertains. Although any methods and materials similar or equivalent to those described herein can be used in the practice or testing of the present invention, the preferred methods and materials will now be described. All publications mentioned hereunder are incorporated by reference. In addition, the materials, methods and examples are illustrative only and not intended to be limiting.

The methods of the present invention provide rapid, efficient, easily automated assays that can be used to directly assess whether a germ-line mutation in a gene which is a transcriptional regulator results in the production of a non-functional gene. They are especially effective in detecting point mutations, such as missense and nonsense mutations.

Implementation of any of these methods would be particularly efficacious for screening individuals who are thought to be at an increased risk for developing cancer, e.g., any individual whose familial history demonstrates a higher incidence of cancer than the general population, will thus identify those individuals who should be monitored closely in order to facilitate early detection and treatment of tumors.

Other features and advantages of the invention will be apparent from the following description and from the claims.

DETAILED DESCRIPTION

The drawings will first be briefly described.

BRIEF DESCRIPTION OF THE DRAWINGS

TUMOR SUPPRESSORS

The tumor suppressor function of at least some genes, such as the retinoblastoma gene (Rb), Wilm's tumor gene (WT1) and p53, has been attributed to the ability of their gene products to regulate the transcription of cellular genes. This ability has been ascribed, at least in part, to the association, directly or indirectly, of the protein products of these genes with specific DNA sequences found in the upstream regulatory region of some cellular genes. For example, recent studies have demonstrated that the p53 polypeptide binds to specific DNA sequences (Fields et al., *Science* 249:1046, 1990; Raycroft et al., *Science* 249:1049, 1990; Kern et al., *Science* 252:1708; El-Deiry et al., *Nature Genetics* 1:45, 1992; Funk et al., *Mol. Cell. Biol.* 12:2866, 1992; Farmer et al., *Nature*, 358:83, 1992). The functional importance of this DNA binding activity has been demonstrated by the ability of the wild-type p53 protein to activate the transcription of recombinant promoters containing these sequences. In patients with germline p53 mutations, both wild-type and mutant alleles are expressed in normal cells. Therefore, the direct analysis of the transcriptional activity of tumor suppressor genes expressed in normal cells should allow the detection of inactivating germline mutations.

In general, the method of the invention involves constructing a reporter plasmid by inserting the DNA sequence to which the tumor suppressor polypeptide is able to directly or indirectly bind upstream from a promoter controlling the expression of a gene encoding a detectable protein such as β-galactosidase, chloramphenicol acetyl transferase, an enzyme which is essential for cell viability (e.g., for the biosynthesis of an essential amino acid), or a protein which confers antibiotic resistance. If the tumor suppressor protein stimulates transcription, the DNA binding site can be directly cloned into an eukaryotic expression vector which contains a promoter which produces little, if any detectable protein, e.g., the plasmid pFosΔLacZ which contains a deletion mutant of the murine fos promoter, the open reading frame of the LacZ gene, the small t intron and the polyadenylation signals of SV40. If the tumor suppressor protein is able to repress transcription, the DNA binding site can be cloned upstream of an active promoter controlling the expression of the LacZ protein (e.g., β-actin). The next step is the stable transfection of cDNA encoding both alleles of the tumor suppressor gene obtained from cells of an individual into cultured cells, e.g., Saos-2 or yeast which contain the reporter plasmid in either autonomously replicating form or integrated into the genome. Alternatively, the reporter plasmid and CDNA may be cotransfected, or may even be manipulated by standard techniques to be contained within one vector. The final step is the analysis of the presence of detectable protein in transfected cells.

There now follows examples which describe the use of the method of the invention to detect germline mutations which inactivate the transcriptional function of p53. These examples are for illustrative purposes and are not intended to be limiting.

EXAMPLE 1

Analysis of p53 transcriptional activity in mammalian cells

Plasmids

Two copies of the oligonucleotide GGAAT TCCTT GCCTT GCCTG GACTT GCCTG GCCTT GCCTT GGAAT TCC (SEQ ID NO:1) were cloned into the EcoRI restriction site of the pBSK (Stratagene, Inc.) plasmid to generate the plasmid pBSK(RGC). This oligonucleotide contains the region from nucleotide 103 to nucleotide 134 of fragment A isolated by Kern et al. (*Science* 252:1708). This fragment A contains the p53 binding site located in the Ribosome Gene Cluster (RGC) (Kern et al., *Science* 252:1708; Farmer et al. *Nature* 358:83, 1992). A 3.6 kb HindIII-KpNI restriction fragment containing the murine for promoter (a 165 bp HindIII-XbaI restriction fragment from the plasmid pfosCATΔ56 (Gilman et al., *Mol. Cell. Biol.* 6:4305, 1986)), the open reading frame of the LacZ gene (a 3106 bp XbaI-BamHI restriction fragment), the small t intron and the polyadenylation signals of SV40, was then cloned into the plasmid pBSK SK(RGC) to generate the plasmid pRGCFosΔLacZ. The plasmid pFosΔLacZ differs from the plasmid pRGCFosΔLacZ by the absence of the RGC fragment.

The wild-type p53 protein, the mutant protein at codon 143, and the mutant protein at codon 273 were respectively expressed by the plasmids pC53-SN3, pC53-SCX3 (Baker et al., *Science* 249:912, 1990) and PSVXRI (Diller et al., *Mol. Cell. Biol.* 10:5772, 1990). In addition, vectors expressing the mutant proteins at codons 181, 245, 248, 258, 282 have been previously described (Frebourg et al., supra). The vector expressing the mutant protein at codon 249 observed in hepatocellular carcinoma (Bressac et al., *Nature* 350:429, 1991; Hsu et al., *Nature* 350:427, 1991) was constructed using oligonucleotide-directed mutagenesis of the p53 cDNA in the phage M13mp19 with an Amersham cDNA synthesis kit. All the p53 expression vectors except the pSVXRI plasmid are derived from the pCMV-Neo-Bam vector (Baker et al., supra).

Amplification and cloning of p53 cDNA

Total RNA were extracted from fibroblasts or lymphocytes using the rapid acid phenol extraction procedure (Sambrook et al., *Molecular cloning. A laboratory manual.* Cold Spring Harbor Laboratory Press, 1989). Reverse transcription was performed using 2–5 μg of total RNA and the Pharmacia reverse transcription kit (First-Strand cDNA Synthesis Kit). p53 cDNA were specifically amplified from half of the reverse transcription reaction using the primers: Sense, 5' AGTCA AGCTT GACGG TGACA CGCTT CCCTG GATT 3' (SEQ ID NO:2) and antisense, 5' AGTCT CTAGA TCAGT GGGGA ACAAG AAGTG GAGA 3' (SEQ ID NO:3). These primers contain HindIII and XbaI restriction sites to facilitate cloning and correspond to p53 sequences located upstream the ATG initiation codon and downstream the TGA stop codon, respectively. The PCR fragments after digestion with HindIII and XbaI were purified on low melt agarose and cloned into the corresponding sites of the pJ7Ω vector. In this vector, the CDNA are under the transcriptional control of the CMV enhancer/promoter.

Cell culture and transfection

The Saos-2 and KHOS-240S cell lines were obtained from the American Type Culture Collection. These cell lines are derived from human osteosarcomas (Diller et al., supra). In the Saos-2 cell line, both p53 alleles are deleted and the KHOS-240S cell line contains only one p53 allele with a mutation at codon 156 (Arg→Pro) (Romano et al., Oncogene 4:1483, 1989). Early passage fibroblasts derived from skin biopsies were also obtained. All cells were grown as previously described (Diller et al., supra). The reporter plasmid pRGCFosΔLacZ (10 µg) was cotransfected with p53 expression vectors using the calcium-phosphate procedure into Saos-2 cells at 70% confluence in 10 cm plates. To test the pRGCFosΔLacZ plasmid, 10 µg of the vectors expressing the wild-type protein or the mutant proteins at codons 143, 181, 245, 248, 249, 258, or 282 were used. For the analysis of the p53 vectors derived from the cDNA amplification, plasmid DNA was purified form 1.5 ml of confluent bacterial culture using the alkaline lysis minipreparation procedure (Sambrook et al., supra). Ninety percent of the DNA minipreparation were used for the transfection.

Analysis of the β-galactosidase activity

The β-galactosidase activity of cells transfected with the reference p53 expression vectors was analyzed using standard methods (Sambrook et al., supra). The enzymatic reaction were performed for 30 min at 37° C., and measured on a spectrophotometer at 420 nm. To measure the transcriptional activity of p53 vectors derived from the cDNA amplification, we used a modification of the standard protocol. Cells were collected 48 h after the transfection in 1.5 ml of Tris-Hcl pH8 50 mM, NaCl 150 mM, EDTA 1 mM. After centrifugation 30 seconds at 10000 rpm, the cells were resuspended and lysed in 100 µl of 1% digitonin (WAKO) in PBS, 5 minutes at 0° C. The cell lysate was then centrifuged 10 minutes at 10000 rpm at 40° C., and the assay performed on 30 µl of the lysate. The lysate was added to a 96 well plate containing 70 µl of 1.0 mM $MgCl_2$, 45 mM β-mercaptoethanol, 0.88 mg/ml o-nitrophenyl-β-D-galactopyranoside, 47 mM sodium phosphate pH 7.5 per well. The reaction was incubated 15–30 min at 37° C. and then stopped by adding 170 µl of 1M $Na_2CO_3$.

Sequencing reactions

The p53 cDNA molecules were sequenced according to the dideoxy-chain termination method in a thermal cycle using Taq polymerase and fluorescently tagged M13 (−21) universal and reverse sequencing primers. Sequences were analyzed on an Applied Biosystems model 373A automated sequencer.

Results

In order to detect germline p53 mutations which inactivate the transcriptional activity of the wild-type protein, we designed a biological assay composed of 4 steps: (i) Amplification of p53 cDNA from normal cells, (ii) cloning of the p53 cDNA into a eukaryotic expression vector, (iii) transfection of the p53 vectors with a reporter plasmid for the transcriptional activity of p53, into a cell line which does not contain any p53 protein and (iv) analysis of the transfected cells. This assay requires a reporter plasmid which allows easy measurement of the transcriptional activity of p53. To this aim, we constructed the plasmid pRGCFosΔLacZ. This plasmid contains two copies of the RGC-p53 binding fragment in a head to head orientation. The wild-type p53 protein has been shown to bind strongly to this DNA fragment (Kern et al.,Science 252:1708) and this binding activates the transcriptional activity of recombinant promoters containing the RGC fragment (Farmer et al., supra). In contrast, the mutant proteins are unable to bind this sequence and to activate transcription (Farmer et al., supra). In the plasmid pRGCFosΔLacZ, the two RGC fragments are cloned upstream of a deletion mutant of the murine for promoter which has been shown to have no transcriptional activity (Gilman et al., supra). Cotransfection experiment using the pRGCFosΔLacZ plasmid and a wild-type p53 expression vector into Saos-2 cells results in approximately a 50 fold stimulation in the β-galactosidase activity (Table 1). In contrast, transfection experiments with the plasmid pFosΔLacZ which does not contain the RGC fragment showed that the transcriptional activity of the for promoter is very weak in Saos-2 cells and that this activity is not inducible by the p53 protein (Table 1). Cotransfection experiments with the pRGCFosΔLacZ plasmid and vectors expressing mutant proteins at codon 143, 245, 248, 249, 258, 273, and 282, showed that these mutant p53 proteins were unable to activate the transcription of the RGC-for promoter. In contrast, cotransfection of the reporter plasmid with a vector expressing the mutant at codon 181 (a functionally silent mutation without biological significance (Frebourg et al., supra) revealed that the 181 mutation had not inactivated the transcriptional activity of the p53 protein (Table 1).

TABLE 1

Transactivation of the pRGCFosΔLacZ plasmid by p53

|  |  | EXP. 1 | EXP. 2 |
|---|---|---|---|
| pRGCFosΔLacZ + | pCMV-Neo-Bam | 2.5 | 1.8 |
|  | wild-type p53 | 100 | 100 |
|  | mutant 143 (Val->Ala) | 0.4 | 1.9 |
|  | mutant 181 (Arg->His) | 242 | 300 |
|  | mutant 245 (Gly->Cys) | 1.7 | 1 |
|  | mutant 248 (Arg->Trp) | 3.7 | 1.1 |
|  | mutant 249 (Arg->Ser) | 1 | 1.2 |
|  | mutant 258 (Glu->Lys) | 1.1 | 1.1 |
|  | mutant 273 (Arg->His) | 1.7 | 1.3 |
|  | mutant 282 (Arg->Trp) | 13.6 | 2.9 |
| pΔFosLacZ + | pCMV-Neo-Bam | 1.9 | |
|  | wild-type p53 | 0.4 | |

These results indicate that the pRGCFosΔLacZ plasmid is a convenient reporter plasmid to specifically detect mutations which inactivate the transcriptional activity of p53.

Figure 1:
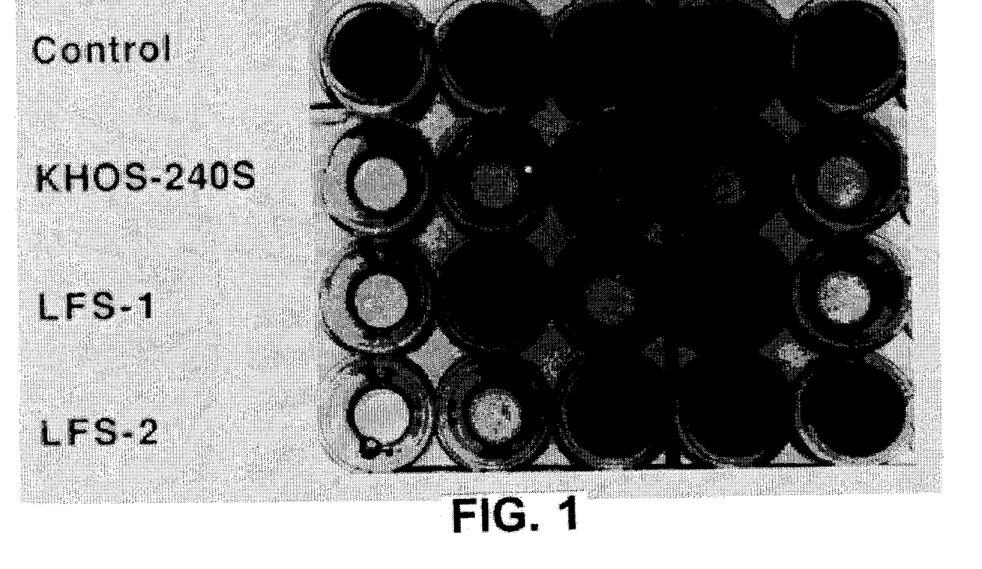
FIG. 1 is a photographic representation of the detection of p53 mutations in CDNA obtained from cell samples.

We then analyzed the transcriptional activity of p53 proteins expressed in normal cells from patients. The p53 cDNA derived from total RNA were specifically amplified and cloned into the eucaryotic expression vector pJ7Ω. For every sample, 4 to 6 individual minipreparations of plasmid DNA were then cotransfected into the Saos-2 cells with the pRGCFosΔLacZ plasmid. We simplified the standard β-galactosidase assay to easily be able to detect the transcriptional activity of p53 vectors purified according to DNA minipreparation procedure. Transfected cells were lysed in 1% digitonin and the assay was performed in a small volume in a 96 well plate for 30 min. at 37° C. As illustrated in FIG. 1 (Lane 1, lymphocytes from a normal individual; lane 2, KHOS-240S cells; lane 3, fibroblasts from a patient with LFS; lane 4, fibroblasts from a patient with LFS), a yellow color indicates that the p53 cDNA is wild-type; a white color indicates that the CDNA contains a mutation which has inactivated the transcriptional activity of the protein. These results showed that 5 individual p53 vectors derived from a normal individuals had wild-type p53 transcriptional activity. This indicated that the predicted genotype of this individual is WT/WT. In contrast, the same analysis performed on an osteosarcoma cell line (KHOS-240S) showed that none of the clones had a detectable transcriptional activity confirming that the predicted genotype was mutant (FIG. 1). We then analyzed fibroblasts from two LFS patients. The transcriptional assay revealed that 2/5 clones and 3/5 clones had a transcriptional activity, respectively. Therefore, the predicted genotype in both cases was WT/mt (FIG. 1). Sequencing analysis of the specific p53 clones without any transcriptional activity indicated that one patient had a p53 allele with a mutation at codon 248 (Arg→Gln), and the other had a p53 allele with a mutation at codon 193 (His→Arg).

EXAMPLE 2

Analysis of p53 transcriptional activation in yeast
Strains and media

The protease deficient strain GA71 was used throughout (genotype Mata leu2 trpl ura3-52 prbl-1122 prcl-407 pep4-3). The strain (previously called BJ2169) was obtained from S. Gasser and created by E. Nones. Routine manipulation of yeast was carried out as described (Guthrie and Fink, (1991) *Meth Enyzymol* 194). Plasmids were transfected into yeast by electroporation (Guthrie and Fink supra). For induction of p53 expression strains were grown overnight in 2% raffinose minimal medium and transferred to 2% galactose minimal medium five and a half hours before harvesting. Unless stated otherwise yeast were grown at 30°.
Plasmids Plasmids were constructed using standard techniques (Sambrook et al. (1989) Molecular cloning: a laboratory manual. Cold Spring Harbor Laboratory Press. New York) and checked for the presence of desired mutations by DNA sequencing using modified T7 DNA polymerase (Sequenase, United States Biochemical).

p53 was expressed in *S. cerevisiae* using P2, a vector containing the GAL1/10 promoter cloned into the ApaI site and the CYC1 terminator cloned into the SacII site of pRS314. pRS314 is a yeast low copy number replicating plasmid containing the TRP1 gene, CEN6 and ARSH4 (Sikorski and Hieter (1989) *Genetics* 122:19–27). p53 cDNAs containing various mutations were derived from bacterial expression plasmids constructed by Midgely et al. (Midgely et al. (1992) *J Cell Sci* 101:183–189). The human p53 cDNAs as XbaI/HindIII fragments into SpeI/NotI digested P2. The 5'-untranslated region in the p53 mRNA contains 55 nucleotides of the GAL1 mRNA followed by 5' CCCCGGATCC ACTAGAAATA ATTTTGTTTA ACTT-TAAGAA GGAGATATAC GC-ATG-3' (SEQ ID NO:4) in the plasmids expressing the human 175H, 248W and 273H cDNAs. In plasmids expressing the human wild type and 285K cDNAs the underlined A is replaced by CCCCTCGA (SEQ ID NO:5). In the plasmids expressing murine p53 the underlined GC is replaced by AT.

Figure 2:
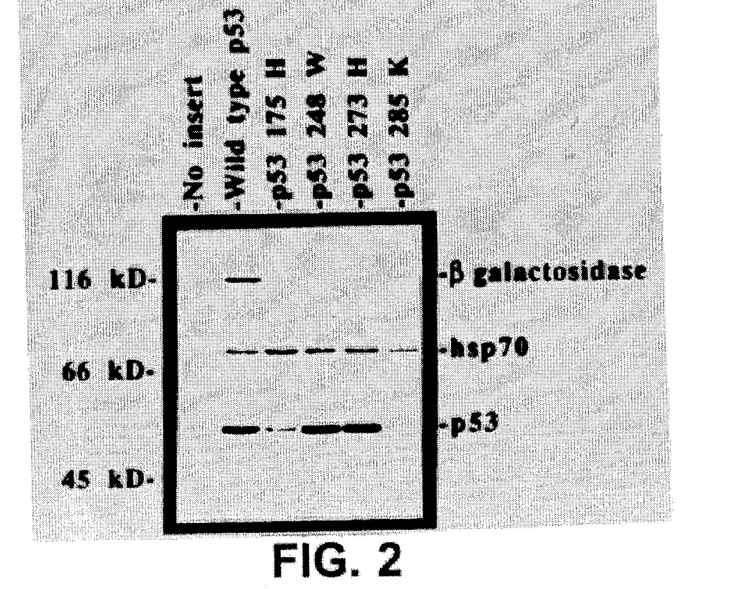
FIG. 2 is an immunoblot of yeast probed with antibodies against p53 (PAb240 and PAb421), hsp70 and β-galactosidase.

The transcription reporter plasmids contain the URA3 gene, the 2 μ replication origin and the *E. coli* LacZ gene coding sequence fused to the *S. cerevisiae* CYC1 gene transcription control elements (Guarente and Mason (1983) *Cell* 32:1279–1286). pLGΔ312 contains the complete CYC1 upstream region ('intact CYC1 promoter'); pLGΔ178 contains a truncated version lacking the upstream activating sequences ('minimal promoter'). There is a XhoI site at the 5'-end of the promoter in pLGΔ178 into which DNA fragments can be cloned to test them for enhancer activity. A double-stranded oligonucleotide adaptor with the sequence 5'-TCGA-CCTTGCCTGGAC-TTGCCTGGCCTTGCCTTT-TCGA-3' (SEQ ID NO:6) (Kern et al. (1991) *Science* 252:1708–1711) was cloned into the XhoI site in pLGΔ178 and a set of plasmids containing different multimers and orientations of the adaptor was obtained. For the experiments presented in table 2, a single copy of the adaptor with the indicated 3'-end adjacent to the CYC1 promoter was used ('orientation-1'). For Table 3, orientation-1 was used in the constructs marked "1, 2, 3 copies p53 oligo"; the adaptor was reversed (i.e., with the indicated 5'-end adjacent to the CYC1 promoter, 'orientation-2') in the construct "1 copy p53 oligo*"; the palindrome construct contains two copies of the adaptor with the indicated 5'-end in the middle of the palindrome. For table 4 and FIG. 2, a single copy of the adaptor in orientation-2 was used.
Antibodies PAb240 (Gannon et al. (1990) *EMBO J* 9:1595–1602), PAb246 (Yewdell et al. (1986) *J Virol* 59:444–452), PAb1620 (Ball et al. (1984) *EMBO J* 3:1485–1491; Hebel et al. (1986) *Z Naturforsch C* 41:94–99; Milner et al. (1987) *Oncogene* 1:453–455) and PAb421 (Haarlow et al. (1981) *J Virol* 39:861–869) are mouse monoclonal antibodies against p53. CM1 is a rabbit polyclonal antibody against p53 (Bartek et al. (1991) *Oncogene* 6:1699–1703). BG2 (D. Lane), PAb204 (Lane and Hoeffler (1980) *Nature* 288:167–170) and 7.10 (S. Lindquist) are monoclonal antibodies against β-galactosidase, SV40 T antigen and hsp70, respectively.

Figure 3:
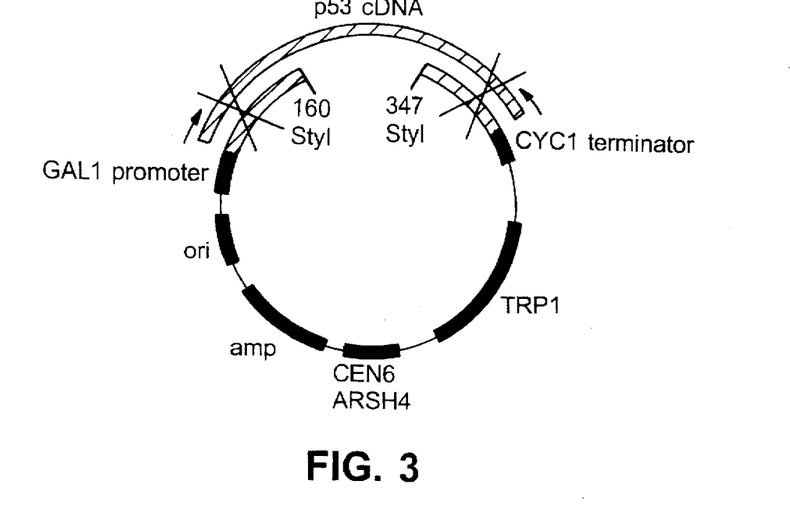
FIG. 3 is a diagram depicting the DNA molecules transfected into yeast for the gap repair assay described in Example 2.

Immunoprecipitation and immunoblotting were performed as described (Harlow and Lane (1988) Antibodies: A laboratory manual. Cold Spring Harbor Laboratory Press, New York). Cells were lysed by vortexing for 1 minute with acid-washed glass beads in 150 mM NaCl, 50 mM Tris pH8.0, 5 mM EDTA, 1 mM DTT and 0.1 mg/ml PMSF. NP40 was then added to a final concentration of 1% and the extract was left on ice for 15 minutes. After clarification by centrifugation at 100,000×g for 15 minutes the extract was preabsorbed with Protein G-Sepharose beads (Pharmacia) for 30 minutes. The extract was divided into equal aliquots and monoclonal antibody-coated Protein G beads were added. After incubation at 40° for one hour beads were collected by centrifugation, washed three times in lysis buffer and resuspended in SDS gel sample buffer. For immunoblotting without prior immunoprecipitation cells were resuspended in 150 mM NaCl, 50 mM Tris pH 8.0, 1% NP40, 0.5% Na deoxycholate and 0.1% SDS, lysed with glass beads, and an equal volume of 2×SDS gel sample buffer was added.
β-galactosidase assays β-galactosidase assays were performed as described (Miller, J. H. (1972) Experiments in molecular genetics. Cold Spring Harbor Laboratory. Cold Spring Harbor, N.Y.) using SDS/chloroform lysis. $10^7$ cells were incubated with o-nitrophenyl-β-D-galactopyranoside (ONPG) for 5 minutes. Samples were spun at 10,000×g for 5 minutes to remove debris before measurement of OD. Results are expressed as ($1000 \times A_{420}$) per minute after deduction of the absorbance of a control sample lacking ONPG. For analysis of temperature sensitive mutants cells were not preincubated on ice. Each value is the mean of three assays±standard deviation.
Gap repair assay The recipient strain for the gap repair experiments was initially transfected with a pLGΔ178-derived lacZ reporter plasmid containing 3 copies of the p53 DNA-binding site adaptor oligonucleotide (in orientation-1, see above). 1 ng of the human wild type and 273H mutant p53 cDNA plasmid proSp53 (Matlashewski et al. (1987) *Mol Cell Biol* 7:961–963) and pR4.2 (Harlow et al. (1985) *Mol Cell biol* 5:1601–1610) were amplified for 30 cycles (92° for 30", 60° for 30", 72° for 150") with 2 units AmpliTaq DNA polymerase in buffer containing 10 mM Tris pH 8.3, 50 mM KCl, 1.5 mM MgCl$_2$, 0.1% Triton-x100, 200 µM deoxynucleotides, 10% dimethyl sulfoxide, 100 µM tetramethylammonium chloride and 5 µg/ml primers, and the products were extracted with chloroform and precipitated with ethanol. The polymerase chain reaction (PCR) primers used were 5'-TGGATTGGCAGCCAGACTGCCTTCC-3' (SEQ ID NO:7) (11 nucleotides before the initiator methione codon) and 5'-GTGGGAGGCTGTCAGTGGGGAACAA-3' (SEQ ID NO:8) (14 nucleotides after the stop codon). The yeast expression plasmid containing the human p53 175H mutant (described above) was digested with StyI and the vector fragment (codons 160 to 347, see FIG. 3). The gapped plasmid and PCR products overlap by 477 base pairs at the 5'-end and 280 base pairs at the 3'-end. Approximately 100 ng of the gapped plasmid was mixed with ~500 ng of PCR product, transfected by electroporation into the strain containing the lacZ reporter plasmid and 1/100th of the transfection mix was spread on plates containing 1M sorbitol, 2% glucose, 0.67% yeast nitrogen base (Difco), 1% casaminoacids (Difco) and 2.5% agar (Difco). To detect β-galactosidase activity individual colonies were streaked onto plates containing 40 mg/l X-gal (Sigma), 0.1M phosphate buffer pH 7.0, 2% galactose, 0.67% yeast nitrogen base (Difco), 1% casaminoacids (Difco) and 2.5% agar (Difco).

Results

The ability of p53 to activate transcription was tested by cotransfecting yeast with a p53 expression plasmid and lacZ reporter plasmids (Table 2). The positive control contains the intact CYC1 promoter fused to the lacZ gene coding sequence.

TABLE 2

| | | β-galactosidase assays. | |
|---|---|---|---|
| Expression plasmid | lacZ reporter plasmid | Glucose | Galactose |
| No insert | Intact CYC1 promoter | 180 ± 14 | 546 ± 23 |
| Wild type human p53 | Intact CYC1 promoter | 205 ± 27 | 523 ± 20 |
| No insert | Minimal promoter | 1 ± 1 | 1 ± 1 |
| Wild type human p53 | Minimal promoter | 1 ± 1 | 2 ± 2 |
| No insert | p53 CYC1 promoter | 1 ± 1 | 3 ± 1 |
| Wild type human p53 | p53 CYC1 promoter | 1 ± 1 | 139 ± 1 |

Units of β-galactosidase were calculated as described in the methods section and represent the mean of three independent assays ± standard deviation. The intact CYC1 promoter is mildly repressed by glucose (Guarente and Ptashne (1981) Proc Natl Acad Sci USA 78: 2199–2203).

Truncation of this promoter at the XhoI site removes upstream activating sequences which normally control the activity of the CYC1 promoter ('minimal promoter'). The test promoter ('p53::CYC1 promoter') contains a 33 base pair p53 DNA-binding sequence (Kern et al. supra) cloned into the XhoI site of the minimal promoter. The p53 expression plasmid contains a wild type human p53 cDNA under the control of the GAL1 promoter:p53 expression is repressed by glucose and stimulated by galactose. Table 2 shows that p53 stimulates lacZ expression, and that the effect requires both the presence of p53 protein (compare glucose with galactose) and the presence of the p53 DNA-binding site (compare the minimal promoter with the p53::CYC1 promoter). The effect of orientation and copy number of the 33 base pair sequence on wild type human p53-dependent transcription were analyzed (table 3).

TABLE 3

| β-galactosidase assays using different multimers and orientations of the p53-binding oligonucleotide. | | |
|---|---|---|
| lacZ reporter plasmid | Glucose | Galactose |
| Minimal promoter | 2 ± 1 | 1 ± 1 |
| Intact CYC1 promoter | 228 ± 9 | 340 ± 19 |
| 1 copy p53 oligo | 3 ± 1 | 98 ± 8 |
| 2 copies p53 oligo | 2 ± 2 | 338 ± 42 |
| 3 copies p53 oligo | 2 ± 1 | 639 ± 63 |
| 1 copy p53 oligo* | 2 ± 1 | 441 ± 54 |
| Palindrome p53 oligo | 3 ± 1 | 653 ± 28 |

*The orientation of the oligonucleotide was reversed in this construct.

Transcription from a single copy is four-fold more effective in one orientation than the other, and is strongly dependent on the number of copies of the binding site oligonucleotide.

The ability of human p53 mutants to stimulate transcription was tested with the reporter plasmid containing a single copy of the binding site oligo in the more effective orientation. Four mutants were examined (175H, 248W, 273H and 285K). Amino acids 175, 248 and 273 are hotspots for mutation in human tumors (Levine et al. (1991) *Nature* 351:453–456). Amino acid 248 is commonly mutated in the Li-Fraumeni hereditary cancer syndrome (Malkin et al. (1990) *Science* 250:1233–1238). The 175H mutant cooperates efficiently with ras in transformation assays and binds to hsc70, whereas the 273H mutant cooperates the inefficiently with ras and fails to bind to hsc70 (Hinds et al. (1990) *Cell Growth and Differentiation* 1:571–580). The 285K mutant was chosen because it binds well to the mutant p53-specific antibody PAb240 and fails to bind to the wild type p53-specific antibody PAb1620 in immunoprecipitation assays using mammalian cell extract (Bartek et al. (1990) *Oncogene* 5:893–899). Three of the mutants (175H, 248W and 273H) are completely inactive in transcription assays in yeast whereas the fourth mutant is weakly active (285K, table 4).

TABLE 4

| β-galactosidase assays using different p53 mutants. | | |
|---|---|---|
| Human p53 gene | Minimal promoter | p53 CYC1 promoter |
| wild type | 3 ± 1 | 334 ± 13 |
| 175H | 2 ± 2 | 3 ± 1 |
| 248W | 3 ± 1 | 2 ± 1 |
| 273H | 3 ± 1 | 3 ± 1 |
| 285K | 3 ± 1 | 24 ± 4 |

Cells were grown in medium containing galactose.

The inactivity of the mutants does not result from a general inhibition of transcription or failure to enter the nucleus. All of the mutants express detectable amounts of p53 protein (FIG. 2), although the level of the 175H and 285K mutants is lower than that of wild type p53, presumably due to instability of the mutant protein. Since the 285K mutant is partially active despite its low level of expression the inactivity of the 175H mutant can not be due solely to its low, but comparable level of expression.

The correlation between mutation and transcriptional inactivation suggests that it should be possible to detect p53 mutation using a simple yeast colony colour assay. Yeast will repair double stranded breaks in transfected plasmids by homologous recombination i.e, 'gap repair' (Guthrie and Fink supra). If yeast are transfected with both a gapped plasmid and a suitable linear template they use the transfected template to repair the gap. It is thus possible to cotransfect yeast with a fragment of p53 cDNA and a gapped p53 expression plasmid (FIG. 3), select for the auxotrophic marker on the plasmid and test colonies for β-galactosidase activity on X-gal plates. To test this strategy, wild type and 273H mutant p53 CDNA plasmids (proSp53 and pR4.2) were amplified by the polymerase chain reaction using primers which span the open reading frame and cotransfected with a gapped expression plasmid into yeast containing a lacZ reporter plasmid. Non-homologous repair and integration events are expected to give rise to a small number of colonies in transfections with plasmid alone. Addition of the p53 PCR product produced a 75-fold increase in the number of colonies relative to that seen the gapped plasmid alone. 35 randomly picked colonies from the primary transfection plates were transferred to plates containing galactose and X-gal to induce p53 expression and assay β-galactosidase activity. All colonies from the plate transfected with plasmid alone were white. One out of 35 colonies transfected with the 273H mutant was blue, and 30 of 35 colonies transfected with the wild type PCR product were blue.

This example demonstrates that p53 can function as a transcription factor in yeast. In addition, the gap repair assay should facilitate the detection of p53 mutations in tumors because it lends itself readily to the analysis of large numbers of samples: transfecting yeast directly with p53 PCR products avoids the difficulties associated with direct sequencing and the additional steps required for subcloning in bacteria are avoided.

EXAMPLE 3

Separation and Analysis of p53 alleles in yeast

Yeast strain and media

The strain YSS1 (MATa ade2-1 his3-11 trp1-1 leu2-3,112 ura3-1 can1-1 pep4::URA3) was obtained from S. Gasser. The plasmid pSS1 that contains TRP1 gene, was introduced into ySS1, and this transformant was used in this experiment as the strain ySS5. Basic methods for yeast manipulation was carried out as described above. Liquid media contained 0.67% yeast nitrogen base, 2% dextrose, 1% casamino acids and 20 µg/ml of adenine (SDA cas). Solid media for auxotrophic section of appropriate plasmids contains 067% yeast nitrogen base, 2% dextrose, 20% agar with complete additions except for auxotrophic markers (SC -leu, S,C -his-leu).

Transformation of yeast

For one transformation, overnight culture of yeast cells were diluted to an $A_{600}$ of 0.2 in 10 ml of SDAcas liquid media, then grown to an $A_{600}$ of 0.6–1.0 at 30° C. The cells were pelleted by centrifugation, and then washed in 1 ml LiOAc solution (0.1M lithium acetate, 10 mM Tris HCl, 1 mM EDTA Na$_2$, pH7.5). After centrifugation, cells were resuspended in 50 µl of LiOAc solution. These LiOAc treated cells were added to a 1.5 ml-tube containing p53 expression vector with 50 µg of carrier DNA, followed by the addition of 300 µl of LiOAc solution containing 40% of polyethylene glycol 3350-4000. This mixture was incubated at 30° C. for 30 min with shaking, and then at 42° C. for 15 min. For the gap repair assays, 50–100 ng of the gapped vector and 50–200 ng of p53 cDNA (a restriction fragment digested from a plasmid or PCR product) were introduced instead of the p53 expression vector. The cells were collected, resuspended in 70–100 µl of sterile H$_2$O, and then spread onto a plate SC-leu. These conditions generated between 100 and 3000 Leu$^+$ colonies after incubation for 36–40 hours at 30° C., depending on the transformation efficiency. Some of the colonies (usually 50 colonies) were re-plated on SC -his -leu and further incubated for 48 hours at 37° C., and the number of colonies which grew on the plate (His$^+$, Leu$^+$ phenotype) were counted.

RT-PCR

Messenger RNA was extracted from peripheral mononuclear cells, fibroblasts, cell lines or frozen tumor tissue using a Micro-Fast Track mRNA Isolation Kit Ver. 1.2 (Invitrogen). cDNA was synthesized from part of the RNA using First-Strand cDNA Synthesis Kit (Pharmacia). To amplify p53 cDNA, 5 µl of first strand cDNA reaction was added to a PCR reaction. The p53 specific primers used were as described in Example 1 (SEQ ID NOS: 1 and 2). PCR was performed in 50 µl of a solution containing 25 mM Tris-HCl pH 8.2, 17 mM KCl, 6 mM (NH$_4$)$_2$SO$_4$, 2.4 mM MgCl$_2$, 180 µM of each dNTP and 2.5 units Pfu polymerase (Stratogene) using a Thermal Cycler (Cetus). To compare the fidelity of reading, 2.5 units of Taq polymerase (Promega) was also used instead of Pfu polymerase where indicated. Time and temperature were programmed for 3 min at 95° C., then 30–35 cycles consisting 1 min at 94° C., 1 min at 58° C., and 2 min at 72° C., followed by 5 min at 72° C. After electrophoresis to evaluate the size of p53 cDNA and the amount of the fragment, the PCR product was introduced into yeast directly or after phenol/chloroform extraction and ethanol precipitation depending on the yield of DNA.

Patient Samples

Peripheral blood samples derived from individuals from high risk families for germline p53 mutation were kindly provided by Frederick P. Li. The lymphocytes were fractionated from whole blood using LeucoPREP (Becton Dickinson) and washed once by ice-cold PBS, pelleted, and then stored at −70° C. until use.

Plasmids, gapped vector and p53 cDNA fragment

Figure 4:
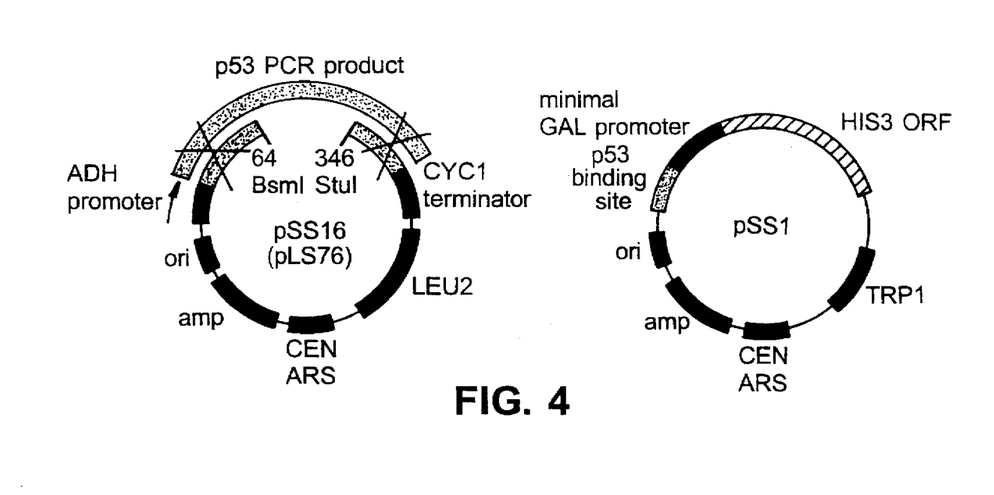
FIG. 4 is a diagram depicting the structure of the p53 expression vector and reporter vector used in Example 3.

The p53 expression vectors pLS76 and pSS16 and the reporter plasmid pSS1 used in this study are shown in FIG. 4.

The NcoI-StuI fragment of p53 cDNA in pLS76(WT) were replaced by mutant (175H, 248W and 273H) human p53 cDNA(s) and called pLS76(175H), pLS76(248W) and pLS76(273H), respectively, which were used as mutant p53 expression vectors. For the gap repair assay, pSS16 was digested with HindIII and StuI, and then the adhesive end of HindIII site was filled in by DNA polymerase (Klenow) followed by dephosphorylation with calf intestinal alkaline phosphatase. After fractionation by agarose gel electrophorecis, the fragment was purified by phenol extraction, precipitated with ethanol, and then redissolved in an appropriate volume of TE. The length of homology in the overlapped regions between p53 cDNA and this gapped vector are 201 and 173 bp at the 5' and 3' ends of p53 cDNA, respectively. A series of human p53 expression vectors for mammalian cells were used for the source of p53 cDNA for the gap repair assay. Wild-type p53 cDNA was isolated from the plasmid pC53-SN3 (Baker et al., 1990 supra). p53 cDNA which encodes mutant proteins at codon 143A, 245C, 248W, 249S, 252P, 258K and 273H were derived from the human p53 expression vectors described above (Example 1). p53 cDNA which encodes mutant proteins at codon 156P, 175H, 248Q and 281E were derived from the pJ7Ω vectors containing each mutant p53 cDNA.

Sequencing analysis

The p53 cDNA(s) were synthesized independently, and then sequenced using Applied Biosystems model 373A automated sequencer, as described above.

Results

This example describes a method which is based on the ability to separate p53 alleles from a patient's p53 cDNA pool using homologous recombination and a gapped p53 excision repair vector. Because homologous recombination is a rare event, it was necessary to set up a method by which to select only for yeast that have successfully accomplished homologous recombination and therefore incorporated a patient's p53 allele into the expression vector. This was achieved using a pSS16 gap excision repair vector (FIG. 4). In its intact circular form, the yeast autonomously replicating sequence (ARS) element allows replication of the LEU2 selectable marker. Since LEU2 is separated from the ARS by the ADH1 promoter driving expression of the p53 cDNA, when a portion of p53 is excised, LEU2 replication will not occur until homologous recombination repairs the gapped sequence. Therefore, when the transformants are plated on SC-leu, it is possible to select for the rare yeast in which the p53 cDNA repairs the gapped sequence by homologous recombination yielding an intact vector (indicated as pLS76 in FIG. 4), when the transformants are plated on SC-leu media. The pSS16 gapped vector also includes a centromere sequence (CEN) to allow the repaired vector, pLS76, to segregate accurately with a single copy during cell division thus producing yeast which contain only a single allele of p53 per cell.

To address questions about transformation efficiency and the potential growth inhibition by different p53 expression constructs, we compared the number of colonies able to grow of SC-leu plates after transformation of yeast with the pLS76 vector containing either wild-type p53, or p53 with mutations at 175H, 248W or 273H. Transformation of yeast with each of these constructs resulted in similar numbers of transformants able to grow on SC-leu plates (3-7×10³ µg of input DNA) (Table 5).

TABLE 5

Transformation of yeast with wildtype or mutant P53 cDNA expression vector

| Input DNA | Transformation efficiency<sup>a</sup> (/ug DNA) | His<sup>+</sup> phenotype<sup>b</sup> % (No. of colonies) |
|---|---|---|
|  | 0 | NA<sup>c</sup> |
| pLS76 (WT) | 4.4 × 10³ | 100 (50/50) |
| pLS76 (175H) | 3.3 × 10³ | 0 (0/50) |
| pLS76 (248W) | 7.1 × 10³ | 0 (0/50) |
| pLS76 (273H) | 3.9 × 10³ | 0 (0/50) |

<sup>a</sup>expressed as the number of Leu<sup>+</sup> colonies per microgram of input DNA.
<sup>b</sup>The part of individual transformants were assayed for His<sup>+</sup> phenotype.
<sup>c</sup>not applicable.

These data suggest similar transformation efficiencies for the different wild-type and mutant p53 constructs. In turn, these experiments also indicate that the level of p53 expressed from the constitutive ADH1 promoter does not significantly effect the growth of these ySS1 strain of yeast.

Selectable transactivation assays for wild-type p53

To alleviate the need to measure an assayable marker, we used a selectable marker that would allow direct selection for yeast containing wild-type p53 activity. This was accomplished using the pSS1 vector (FIG. 4). This vector contains a single p53 binding site as it is present in the ribosomal gene cluster (Kern et al., 1991 supra), upstream of the histidine selectable marker gene. It also contains the tryptophan selectable marker gene so that the construct could be transformed and then maintained in the 35 yeast alleviating the need to cotransfect the vector with the p53 DNA. To examine the fidelity of this selection assay, the yeast were transformed with pLS76 containing either wild-type or mutant p53 cDNA and the His<sup>+</sup> phenotype of the transformants that grew on the SC-leu plates were scored by replica plating them onto both SC-his-leu and SC-leu plates. One hundred percent of the yeast transformed with pLS76(WT) can grow on SC-his-leu plates (Table 5). In contrast, none of the yeast transformed with pLS76 (175H, 248W and 273H) grow on the SC-his-leu plates. Similar assays on seven additional mutant p53s (143A, 156P, 245C, 248Q, 252P, 258K, 281E) were also performed, and none of the yeast containing these p53 mutants grow on the SC-his-leu plates. These results indicate that the His selectable system, which depends on the transcriptional activity of p53, works well to distinguish wild-type from mutant p53 function.

Gap repair assay

Figure 5A:
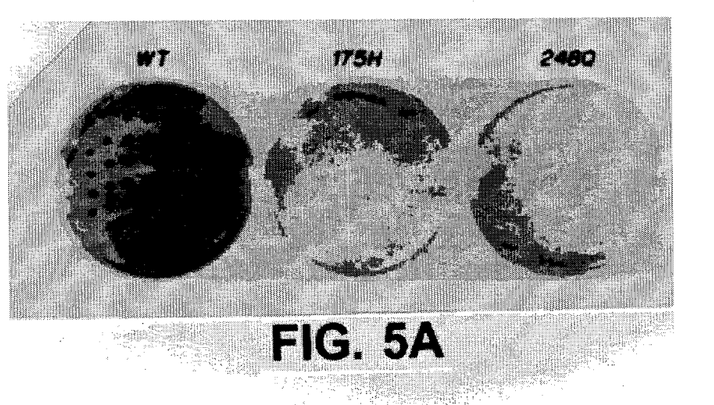
FIGS. 5A and 5B depict auxotrophic selection on SC-his-leu plates of yeast transformed with wild-type or mutant p53 by gap repair assay.
Figure 5B:
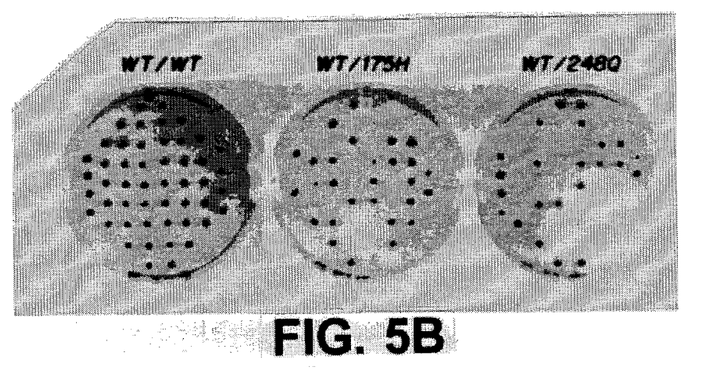

Because germline p53 mutations have been found between codon 71 to 325, the expression vector pSS16 was designed to make the gapped region from codon 67 to 347 (FIG. 5). The efficiency of homologous recombination between this new gapped vector and the p53 cDNA was then tested by determining both the number of colonies that grew on SC-leu plates and the difference in the number of colonies which were able to grow on the SC-his-leu plates for wild-type and mutants p53. When wild-type or mutant p53 cDNA fragments were introduced into the yeast with this gapped vector (p.SS16 HindIII-StuI digest), 2×10²–1.4×10³ colonies were observed on SC-leu plates. In contrast, only 6 colonies were detected in transfection with the gapped vector alone. When the p53 cDNA that was introduced was wild-type, 99.3% (149 of 150) also demonstrated a His<sup>+</sup> phenotype. In contrast, when mutant p53 cDNAs (143A, 156P, 175H, 245C, 248W, 248Q, 252P, 258K, 273H, 281E and 307stop) were introduced, no His<sup>+</sup> colonies were observed (0/50 for each mutant clone). Representative results are shown in FIG. 5. These results indicate that the gapped vector is successfully repaired by homologous recombination with p53 CDNA, and demonstrate that wild-type p53 cDNA can be discriminated from mutant p53 cDNAs by this selectable transactivation system.

Fidelity of PCR product as a template of p53 CDNA

Because the purpose of this assay is to detect germline mutations in patient lymphocytes, RNA must be both reverse transcribed and the cDNA amplified before introduction into yeast. These two techniques are well-known to cause the accumulation of errors which can potentially inactivate p53 function. Therefore, it is necessary to determine the impact of these errors on the use of this assay. The fidelity of RT-PCR was examined by synthesizing p53 cDNA from control lymphocytes. Cotransformation of yeast with this control RT-PCR product amplified by Taq polymerase with a gapped vector resulted in the frequency of His<sup>+</sup> phenotype of only 60% (48–66). To test whether this decrease in His<sup>+</sup> yeast clones was caused by misincorporation introduced by Taq polymerase, we compared the fidelity of Taq polymerase with that of Pfu polymerase. Wild-type p53 cDNA was amplified from a plasmid which contains wild-type p53 cDNA, using Pfu or Taq polymerase at varied concentration of dNTP. After 30 cycles of PCR, the product was introduced into yeast with the gapped vector. Then the His<sup>+</sup> phenotype was evaluated as a marker of the fidelity of the PCR reaction as the phenotype should reflect misincorporation errors in the p53 sequence. As indicated in Table 6 the fidelity of Pfu polymerase was as high as that of pre-PCR template at both 50 and 200 µM of each dNTP.

TABLE 6

Cotransformation of yeast with gapped vector and PCR product of p53 cDNA.

| gapped vector[a] | p53 cDNA (DNA polymerase, each dNTP (μM) | His+ phenotype[b] % (No. of colonies) |
|---|---|---|
| − | — | NA[c] |
| − | non-PCR[d] | NA |
| + | — | 0 (0/3)[e] |
| + | non-PCR | 100 (100/100) |
| + | PCR (Pfu, 50 μM) | 100 (100/100) |
| + | PCR (Pfu, 100 μM) | 100 (100/100) |
| + | PCR (Taq, 50 μM) | 86 (43/50) |
| + | PCR (Taq, 200 μM) | 76 (114/150) |
| + | PCR (Taq, 600 μM) | 42 (26/50) |

[a]plasmid pSS16 HindIII-StuI digest (50 ng)
[b]The part of individual transformants were assayed for His+ phenotype.
[c]not applicable.
[d]wild-type p53 cDNA fragment (100 ng) deribed from pC53SN3
[e]only 3 colonies on SC -leu plate In contrast, the fidelity of Taq polymerase seemed to correlate with the concentration of dNTP in the reaction (86% at 50 μ).

We also examined the RT-PCR product of p53 cDNA prepared from mononuclear cells of a healthy donor. A thirty cycle PCR was performed to amplify the p53 cDNA by Taq or Pfu polymerase in buffer containing 180 μM each dNTP. The fidelity of Pfu polymerase was satisfactory (average 98%) and much higher than that of Taq polymerase (average 66%). Therefore, errors resulting from the RT-PCR step are minimized by using Pfu polymerase.

Detection of germ-line p53 mutations by FASAY

Figure 6:
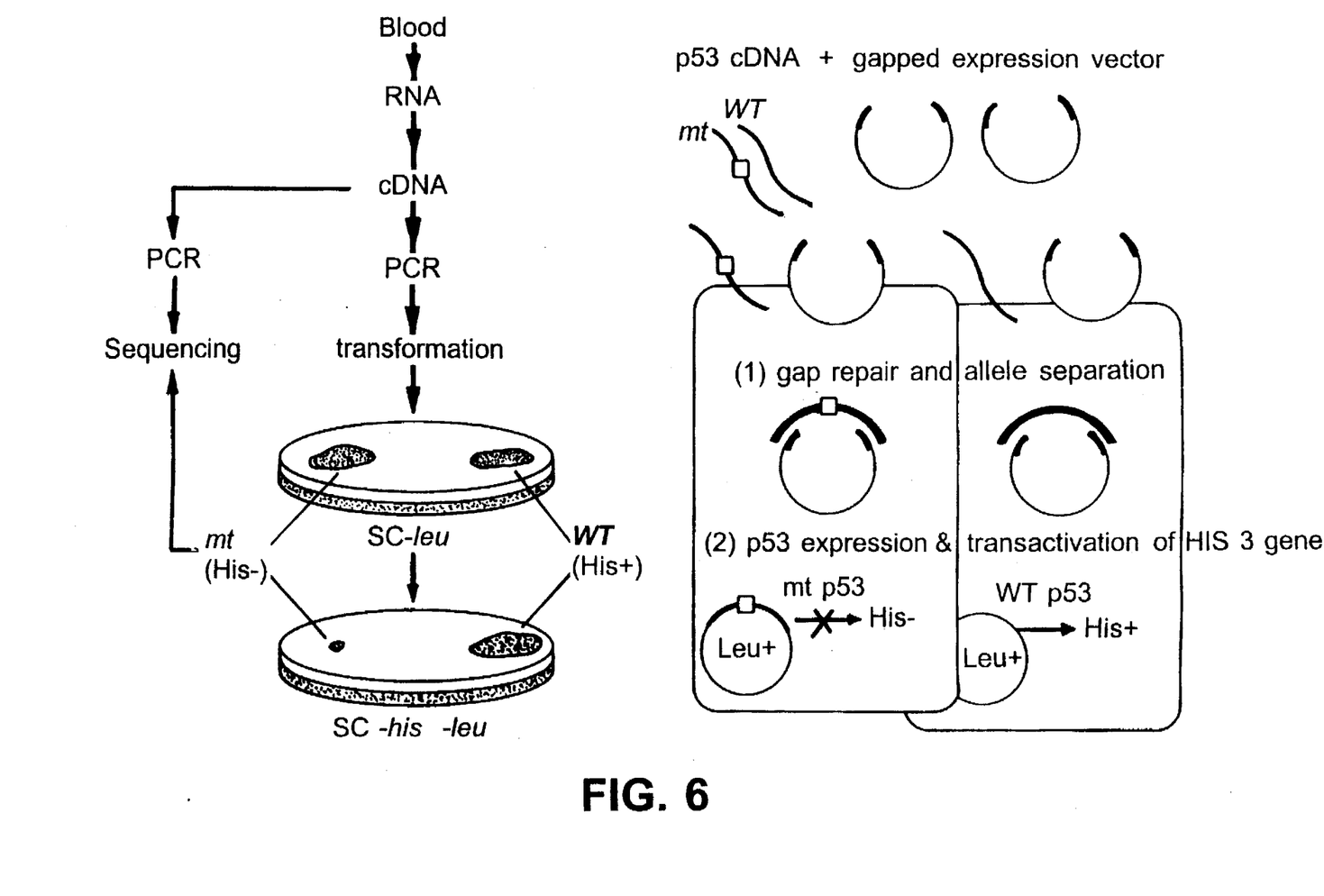
FIG. 6 is a schematic diagram of the functional assay in yeasts

FIG. 6 shows a schematic diagram of FASAY (Functional Assay on Separated Alleles in Yeast) method for detection of heterozygous p53 mutations. To examine whether heterozygous mutations are detectable, lymphocytes from 6 individuals at high risk for germline p53 mutation were analyzed. The p53 cDNA was synthesized using Pfu polymerase and the RT-PCR product containing the p53 cDNA and the gapped pSS16 vector were introduced in yeast by the LiOAc method. Fifty colonies which grew on a SC-leu plate were transferred onto a SC-his-leu plate and examined for a His+ phenotype. The p53 cDNAs from the six individuals were also sequenced bidirectionally using automated sequencer. In 3 out of the 6 individuals (HRP-1, HRP-3 and HRP-5), the predicted p53 genotype were functionally diagnosed at WT/WT, because 98–100% colonies expressed His+ phenotype as observed in the case of a healthy donor (Table 7).

TABLE 7

Cotransformation of yeast with gapped vector and RT-PCR product of p53 cDNA from 6 individuals at high risk families for germline p53 mutations

| Input DNA | | | | |
|---|---|---|---|---|
| gapped vector[a] | p53 cDNA[b] | His+ phenotype[b] % (No. of colonies) | Functional diagnosis | Sequencing analysis |
| − | — | NA[d] | | |
| + | — | NA | | |
| + | healthy donor | 100 (50/50) | WT/WT | NF[e] |
| + | HRP[f] 1 | 98 (49/50) | WT/WT | WT/WT |
| + | HRP 2 | 46 (23/50) | WT/mt | WT/2480 |
| + | HRP 3 | 100 (50/50) | WT/WT | WT/WT |
| + | HRP 4 | 54 (27/50) | Wt/mt | WT/175H |

TABLE 7-continued

Cotransformation of yeast with gapped vector and RT-PCR product of p53 cDNA from 6 individuals at high risk families for germline p53 mutations

| Input DNA | | | | |
|---|---|---|---|---|
| gapped vector[a] | p53 cDNA[b] | His+ phenotype[b] % (No. of colonies) | Functional diagnosis | Sequencing analysis |
| + | HRP 5 | 100 (50/50) | WT/WT | WT/WT |
| + | HRP 6 | 46 (23/50) | WT/mt | WT/273C |

[a,c,d]refer to legend of Table 2.
[b]RT-PCR product
[e]not examined
[f]high risk person In the other 3 members (HRP-2, HRP-4 and HRP-6), approximately 50% (46–54) of colonies have His+ phenotype, predicting a WT/mtp53 genotype. These results corresponded with the sequence data as heterozygous nucleotide changes resulting in amino-acid substitutions 248W (CCG to CAG), 175H(CGC to CAC) and 273C(CGT to TGT) were detected in the HRP-2, HRP-4 and HRP-6 samples, respectively.

DISCUSSION

We have shown that the direct analysis of the transcriptional activity of p53 proteins expressed in normal mammalian cells and yeast allows the detection of germline p53 mutations. The methods described are based on the assumption that significant mutations of the p53 gene inactivate the transcriptional activity of the protein. All the germline p53 mutations described thus far are located in the coding region of the p53 gene and therefore the majority of germ-line mutations should be detectable by these assays. The percentage of false positives identified by these methods are significantly lower than in other techniques since only the mutations which inactivate the transcriptional activity of the protein are detected. These methods are simple, quick, and in one step are able to screen the whole open reading frame of the p53 gene. These assays not only detect mutations but also indicate whether the mutations are functionally significant.

OTHER EMBODIMENTS

Other embodiments are within the following claims.

For example, the method of the invention can also be used as a prognostic indicator in order to promote efficacious treatment of particular tumors. For example, the detection of mutations in p53 in bladder cancer has been shown to correlate with poor clinical outcome (Dalbagni et al. Proc. Am. Assoc. Cancer Res. 33:373, 1992; Sarkis et al., Proc. Am. Assoc. Cancer Res. 33:256, 1992). In addition, an association between clinical prognosis and abnormal Rb gene expression in patients with primary grade sarcomas has been reported (Cance et al., N. Eng. J. Med. 323:1457, 1990). Thus, in cases where a particular tumor is thought to be associated with the inactivation of both alleles of a tumor suppressor gene, the products of both alleles of the tumor suppressor gene can be obtained from tumor cells and analyzed in the method of the invention for functional activity.

Also within the invention are kits which contain the components necessary to carry out the method of the invention. For example, in the case wherein the tumor suppressor gene to be analyzed is p53, a kit might comprise (a) primers such as those described herein (SEQ ID NOS. 2 & 3), (b) a eukaryotic expression plasmid such as pJ7Ω for cloning of the amplified cDNA, (c) a reporter plasmid containing at least one RGC-p53 binding site upstream of a gene encoding detectable protein, e.g., pRGCFosΔLacZ, (d) a frozen aliquot of cells which lack functional p53, e.g., Saos-2 cells, (e) means for assaying for the level of detectable protein in transfected cells, and (f) detailed instructions on how to perform the method of the invention. Alternatively, kits might be designed which contain vectors appropriate for performing the method in yeast cells.

The methods of the invention may also be used to perform a mutational analysis of any other protein which has a detectable biological activity. For example, if a known tumor suppressor gene, such as NFI, has GTP activating protein activity in both humans and yeast, it should be possible to assay the function of the NFI separated alleles from patients by cotransforming with gap excision repair vectors into yeast that lack an ability to grow unless they gain that activity.

What is claim is:

1. A method for determining whether an individual carries a mutation in a gene which encodes a polypeptide which has a DNA mediated biological activity, said method comprising:
   (a) obtaining a first and a second cDNAs from a cell sample from said individual, each of said cDNAs corresponding to an allele of said gene;
   (b) providing a nucleic acid comprising a binding site operably linked to DNA encoding a detectable protein such that the production of said detectable protein is regulated by interaction of said polypeptide with said binding site;
   (c) transfecting said first and second cDNAs and said nucleic acid into yeast cells which naturally express low levels or none of said polypeptide to produce transfected yeast cells, wherein
      i) said first and second cDNAs are cotransfected with a plurality of copies of a gap excision repair vector which comprises a centromere, and
      ii) said transfecting is carried out under conditions which promote homologous recombination of said first and second cDNAs with separate copies of said vector such that said cDNAs are stably incorporated into separate copies of said vector and are transfected into separate cells;
   (d) separating said transfected cells for individual examination; and
   (e) examining the level of said detectable protein in said transfected cells, said level being correlated with the presence of a mutation in at least one of said alleles of said gene.

2. A method for determining whether an individual carries a mutation in one or both alleles of a gene encoding a polypeptide with a detectable biological activity, said method comprising:
   (a) obtaining a first and a second cDNAs from a cell sample from said individual, each of said corresponding to an allele of said gene;
   (b) providing a nucleic acid comprising DNA encoding a detectable protein, wherein the production of said detectable protein is regulated by the wildtype allele of said gene;
   (c) transfecting said first and second cDNAs and said nucleic acid into yeast cells which naturally express low levels or none of said polypeptide to produce transfected yeast cells, wherein
      i) said first and second cDNAs are cotransfected with a plurality of copies of a gap excision repair vector which comprises a centromere, and
      ii) said transfecting is carried out under conditions which promote homologous recombination of said first and second cDNAs with separate copies of said vector such that said cDNAs are stably incorporated into separate copies of said vector and are transfected into separate cells;

(d) separating said transfected cells for individual examination; and (e) examining the level of said detectable protein in said transfected cells, said level being correlated with the presence of a mutation in at least one of said alleles of said gene.

3. The method of claim 1, wherein said polypeptide is a transcriptional regulator.

4. The method of claim 1 or claim 2 wherein said first and second cDNAs are obtained by PCR.

5. The method of claim 4, wherein said cDNAs are obtained by PCR using Pfu polymerase.

6. The method of claim 1 or claim 2, wherein said cell sample comprises normal cells.

7. The method of claim 6, wherein said cell sample is a blood sample.

8. The method of claim 3 wherein interaction of said polypeptide with said binding site activates transcription of the DNA encoding said detectable protein.

9. The method of claim 1 wherein interaction of said polypeptide with said binding site represses transcription of the DNA encoding said detectable protein.

10. The method of claim 1 or claim 2 wherein said polypeptide binds to said binding site.

11. The method of claim 1 or claim 2 wherein said polypeptide is a tumor suppressor.

12. The method of claim 11 wherein said polypeptide is p53.

13. The method of claim 12 wherein said binding site comprises at least one RGC site.

14. The method of claim 1 or claim 2, wherein said level of detectable protein is compared to the level of detectable protein in a standard, and a difference between said levels is indicative that at least one of said alleles from said sample carries a mutation which decreases the biological activity of said polypeptide.

15. The method of claim 1 or claim 2 wherein a difference in the level of said detectable protein between transfected cell samples containing different alleles of said gene is indicative that one of said alleles carries a mutation which decreases the biological activity of said polypeptide.

16. The method of claim 1 or claim 2 wherein said yeast is *Saccharomyces cerevisiae*.

17. The method of claim 1 or claim 2 wherein said detectable protein is an enzyme.

18. The method of claim 17 wherein the activity of said enzyme and said level are determined by calorimetric assay.

19. The method of claim 18 wherein said enzyme is β-galactosidase.

20. The method of claim 17 wherein said enzyme confers resistance to an antibiotic, and said level is determined by the ability of said transfected cells to grow in the presence of said antibiotic.

21. The method of claim 17 wherein said enzyme is essential for the production of a substance required for viability of said transfected cells, and said level is determined by the ability of said transfected cell to grow in the absence of said substance.

22. The method of claim 21 wherein said substance is an amino acid.

23. The method of claim 21 wherein said substance is a vitamin.

24. The method of claim 21 wherein said substance is a purine.

25. The method of claim 21 wherein said substance is a pyrimidine.

26. The method of claim 1 or claim 2 wherein said nucleic acid is stably transfected into said cells prior to transfection with said first and second cDNAs.

27. The method of claim 26 wherein said nucleic acid further comprises a vector which is capable of autonomously replicating within said cells.

28. The method of claim 26 wherein said nucleic acid is integrated into the genome of said cells.

29. The method of claim 1 or claim 2 wherein the presence of said mutation in one of said alleles is an indication that said individual is at increased risk to develop cancer.

30. The method of claim 1 or claim 2 wherein said mutation is a missense mutation.

31. The method of claim 1 or claim 2 wherein said mutation is a nonsense mutation.

* * * * *